US012281359B2

(12) United States Patent
McGovern

(10) Patent No.: US 12,281,359 B2
(45) Date of Patent: Apr. 22, 2025

(54) VARIANTS OF TNFSF15 AND DCR3 ASSOCIATED WITH CROHN'S DISEASE

(71) Applicant: CEDARS-SINAI MEDICAL CENTER, Los Angeles, CA (US)

(72) Inventor: Dermot P. McGovern, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 727 days.

(21) Appl. No.: 17/392,098

(22) Filed: Aug. 2, 2021

(65) Prior Publication Data

US 2021/0371931 A1 Dec. 2, 2021

Related U.S. Application Data

(60) Division of application No. 15/946,632, filed on Apr. 5, 2018, now abandoned, which is a continuation of application No. 14/890,712, filed as application No. PCT/US2014/038468 on May 16, 2014, now abandoned.

(60) Provisional application No. 61/824,932, filed on May 17, 2013.

(51) Int. Cl.
C12Q 1/68 (2018.01)
C12Q 1/6883 (2018.01)

(52) U.S. Cl.
CPC ...... *C12Q 1/6883* (2013.01); *C12Q 2600/112* (2013.01); *C12Q 2600/118* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 9,732,385 | B2 | 8/2017 | Barken et al. |
| 2010/0190162 | A1 | 7/2010 | Rotter et al. |
| 2010/0240043 | A1 | 9/2010 | Rotter et al. |
| 2011/0045476 | A1 | 2/2011 | Barken et al. |
| 2011/0177502 | A1 | 7/2011 | Hakonarson et al. |
| 2013/0344621 | A1 | 12/2013 | Wang et al. |
| 2014/0045276 | A1 | 2/2014 | Singh et al. |
| 2014/0170157 | A1 | 6/2014 | Agarwal et al. |
| 2016/0090629 | A1 | 3/2016 | McGovern |
| 2017/0166967 | A1 | 6/2017 | Rotter et al. |
| 2019/0211400 | A1 | 7/2019 | Rotter et al. |
| 2019/0300957 | A1 | 10/2019 | Gonsky et al. |

FOREIGN PATENT DOCUMENTS

| | | |
|---|---|---|
| AU | 2012254150 A1 | 5/2013 |
| AU | 2012254150 B2 | 8/2015 |
| CA | 2827609 A1 | 11/2012 |
| CA | 2841416 A1 | 12/2012 |
| DK | 2676137 T3 | 1/2015 |
| EP | 2565277 A1 | 3/2013 |
| EP | 2676137 B1 | 12/2014 |
| EP | 2997165 A2 | 3/2016 |
| ES | 2530175 T3 | 2/2015 |
| IL | 227853 A | 7/2017 |
| KR | 20160009582 A | 1/2016 |
| MX | 343327 B | 11/2016 |
| WO | WO-2008106451 A2 | 9/2008 |
| WO | WO-2008106451 A3 | 11/2008 |
| WO | WO-2009052512 A2 | 4/2009 |
| WO | WO-2009105590 A2 | 8/2009 |
| WO | WO-2009105590 A3 | 1/2010 |
| WO | WO-2012154253 A1 | 11/2012 |
| WO | WO-2012174338 A2 | 12/2012 |
| WO | WO-2013059732 A1 | 4/2013 |
| WO | WO-2014186750 A2 | 11/2014 |
| WO | WO-2017106383 A1 | 6/2017 |
| WO | WO-2017161342 A1 | 9/2017 |

OTHER PUBLICATIONS

Aiba et al., The role of TL1A and DR3 in autoimmune and inflammatory diseases. Mediators Inflamm. 2013:#258164, 9 pages.
Chinese Patent Application No. 201480038133.6 Second Office Action dated Jan. 21, 2019.
European Patent Application No. 14797214 Extended European Search Report dated Feb. 3, 2017, 15 pages.
European Patent Application No. 14797214 Partial European Search Report dated Oct. 28, 2016, 9 pages.
European Patent Application No. 17767679.8 Supplementary European Search Report dated Jul. 22, 2019.
European Patent Application No. 18201967.9 European Search Report dated Mar. 6, 2019.
Fransen et al., Inflammatory bowel disease: the genetic background and beyond. University of Groningen PhD Dissertation http://www.rug.nl/research/portal/files/12805965/Complete_dissertation.pdf (2014).
Fuliang et al.: Diagnostics and Therapeutics of Digestive System Diseases. Scientific and Technical Literature Publishing House. 309-310 (2004).
Haritunians et al., Genetic Predictors of Medically Refractory Ulcerative Colitis, Inflamm Bowel Dis., 2010, vol. 16 ;11), pp. 1830-1840.
Hirano et al., Association Study of 71 European Crohn's Disease Susceptibility Loci in a Japanese Population, Inflammatory Bowel Diseases, 19(3):526-533, 2013.
Japanese Patent Application No. 2016-514143 Office Action dated Apr. 2, 2018.

(Continued)

*Primary Examiner* — Jehanne S Sitton
(74) *Attorney, Agent, or Firm* — Wilson Sonsini Goodrich & Rosati

(57) ABSTRACT

Described herein are methods and compositions related to the discovery of associations in TNFSF15 15 and DcR3 genetic loci across in Caucasian, Puerto Rican, and Korean Crohn's Disease, as demonstrated via trans-ethnic fine mapping. The present invention provides methods of quantifying risk and diagnosing susceptibility to Crohn's disease in a subject by determining the presence of one or more risk variants are at the TNF SF15 (or TL1A) and/or DcR3 genetic loci.

5 Claims, 4 Drawing Sheets

Specification includes a Sequence Listing.

(56) References Cited

OTHER PUBLICATIONS

Jostins et al.: Host-microbe interactions have shaped the genetic architecture of inflammatory bowel disease. Nature; 491/7422:119-124 (2012).

Jung et al., Genotype/Phenotype analyses for 53 Crohn's disease associated genetic polymorphisms. PLOS/One, 7(12):e52223, 2012.

Kakuta et al., Su1746 Rare Variants of TNFSF15 are Significantly Associated With Crohn's Disease in Non-Jewish Caucasian Independent of the Known Common Susceptibility SNPs, Gastroenterology, 144(5): S-466, 2013.

Kugathansan et al., Loci on 20q13 and 21q22 are associated with pediatric onset inflammatory bowel disease. Nature Genetics 40:1211-1215 (2008).

Mcgovern et al., Genetics of inflammatory bowel diseases. Gastroenterology 149(5):1163-1176 (2015).

Michelsen et al., IBD-Associated TL 1A Gene (TNFSF15) Haplotypes Determine Increased Expression of TL 1A Protein. PLoS ONE. 4:e4719 (2009).

PCT/US2008/055020 International Search Report and Written Opinion dated Aug. 14, 2008, 8 pages.

Prometheus Biosciences, Inc. Form S-1 Registration Statement as filed with the Securities and Exchange Commission on Feb. 19, 2021 (246 pages).

Picornell et al., TNFSF15 is an ethnic specific IBD gene. Inflamm. Bowel Disease, 13(11):1333-1338, 2007.

Takedatsu et al.: TL1A (TNFSF15) Regulates the Development of Chronic Colitis by Modulating both T helper (TH) 1 and TH17 Activation; Gastroenterology; HHS Public Access; 135(2): 552-567 (2008).

Tong Ren Tang Health Center Editorial Board: Fruity Health Care Dictionary; p. 153 (Jan. 31, 2013).

Tremelling et al., Contribution of TNFSF15 Gene Variants to Crohn's Disease Susceptibility Confirmed in UK Population, Inflammatory Bowel Diseases, 14(6):733-737, 2008.

Wen et al., TL 1A-induced NF-kB activation and c-IAP2 production prevent DR3-mediated C456 apoptosis in TF-1 cells. J Biol Chem 278:39251-39258 (2003).

Yamazaki et al., Single nucleotide polymorphisms in TNFSF15 confers susceptibility to Crohn's disease. Hum Mol Genet 14:3499-3506 (2005).

Yang, Suk-Kyun et al., Association of TNFSF15 with Crohn's Disease in Koreans, American Journal of Gastroenterology 2008;103:1437-1442.

SEQUENCE LISTING

```
<160> NUMBER OF SEQ ID NOS: 26

<210> SEQ ID NO 1
<211> LENGTH: 51
<212> TYPE: DNA
<213> ORGANISM: Homo sapiens
```

```
<220> FEATURE:
<221> NAME/KEY: misc_feature
<222> LOCATION: (26)..(26)
<223> OTHER INFORMATION: n is a, c, g, or t

<400> SEQUENCE: 1
cattttatga gcaatggcat ctggcnatga acgctgctgc ctgaatcaca g          51

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 2
tagctgactt aataaaagaa gtccangcac gaaccttgat gacaatgtga c          51

<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 3
aaaaggtctt ccttaccttc attggntttt gaatgagtga gtaataaact t          51

<210> SEQ ID NO 4
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 4
atagtaatgt tactggcagt gaaccnatgt aggtctatag aatcctcaat t          51

<210> SEQ ID NO 5
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 5
cttaagttcc ccatgaatga cttttncccc ctcctttata aaattgacac c          51

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 6
gtcaatgaac aaaaggccac ataatnatag atttgaaaaa gacctcagag a          51
```

```
<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 7
ggaaccagtt gctacctact tcgcanacag acttggtccc catgaggagc t         51

<210> SEQ ID NO 8
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 8
gaaactgtag actttgctta aaaagngtct catatcattt tcaaaataga c         51

<210> SEQ ID NO 9
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 9
tcaaagtcct aacttatccc agtctngcta tccattattt acttctctct a         51

<210> SEQ ID NO 10
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 10
gggatgagag gtgtgtggtt tgcagnttgg gaaacggaaa tcacatttgc a         51

<210> SEQ ID NO 11
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 11
cattgaccat tgtttaatca gagtangagg ccacagatcg aggtgactgt c         51

<210> SEQ ID NO 12
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t
```

<400> SEQUENCE: 12
gtgatttaga aaaaaaaag agatanaatg atcttaattg caattgaaaa t        51

<210> SEQ ID NO 13
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 13
tgatgatcat ggctaagtgg gacttnagtg actcaaaccc tgtgttcaga t        51

<210> SEQ ID NO 14
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 14
ttggggcctt ttgccccaga agcccntaat tcctcaggcc aacccgaaat t        51

<210> SEQ ID NO 15
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 15
acctgctctt acaagtcacc acctgngagc ctcatgagcc gctggtgtga c        51

<210> SEQ ID NO 16
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 16
gccgctggtg tgacttggac aggacnaagt tgtggcactg tcaccggggt g        51

<210> SEQ ID NO 17
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 17
ctccatcttg gctcagggct ccttgngacc atcttccctg tgcgtccagg t        51

<210> SEQ ID NO 18
<211> LENGTH: 51
<212> TYPE: DNA

```
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 18
gggtcctagg gtcctagacc cctgtnctcc ctgtttctgc ctctgtttgg g        51

<210> SEQ ID NO 19
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 19
actacacgca gttctggaac tacctngagc gctgccgcta ctgcaacgtc c        51

<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 20
cctgccgctg ccgcaccggc ttcttngcgc acgctggttt ctgcttggag c        51

<210> SEQ ID NO 21
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 21
tgccaggctc ttcctcccat gacacnctgt gcaccagctg cactggcttc c        51

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 22
tgagccaggg cacagcctcc cctggngagc tctgggaaag tgggcagcaa t        51

<210> SEQ ID NO 23
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 23
aaggtggctg gctcctctga cacggngaaa ccgaggcctg atggtaactc t        51
```

```
<210> SEQ ID NO 24
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 24
gacctcctcc aggcctccca tgcttnccgg gaagtgaagc ttctccctct c         51

<210> SEQ ID NO 25
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 25
ggtgggagcc ctgcatcagt gatggnggca gtctgcagtc atggtggctt c         51

<210> SEQ ID NO 26
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 26
gcctggggtg tctgggtgca cacctnctcc ccttgctgtg ggggaggctg g         51
```

VARIANTS OF TNFSF15 AND DCR3 ASSOCIATED WITH CROHN'S DISEASE

CROSS-REFERENCE

This application is a divisional of U.S. application Ser. No. 15/946,632 filed Apr. 5, 2018, which is an application is a continuation of U.S. application Ser. No. 14/890,712 filed Nov. 12, 2015, now abandoned, which is U.S. National Stage application of PCT/US14/38468 filed May 16, 2014 which claims the benefit under 35 U.S.C. § 119(e) to U.S. provisional patent application No. 61/824,932, filed May 17, 2013, each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Aug. 2, 2021 is named 56884-721_302_SL.txt and is 6,237 bytes in size.

FIELD OF THE INVENTION

The claimed invention relates to prognosis, diagnosis and treatment of inflammatory bowel disease and related conditions, including methods and compositions for medical therapies.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Inflammatory bowel disease (IBD) such as Crohn's disease (CD) are chronic inflammatory conditions with pathological features such as patchy transmural inflammation and fibrostenosis. Previous studies show that TL1A may drive intestinal inflammation through enhancing Th1, Th2 and Th17 effector function, TL1A appears to also drive fibrogenesis through increased number of fibroblasts and activated fibroblasts and constitutive TL1A expression in mice has been found to confer worsened murine ileo-cecal inflammation, and intestinal fibrostenosis.

SNPs of TL1A (TNFSF15), a TNF superfamily member, have been found to be associated with IBD, and certain TNFSF15 haplotypes have been found to be associated with increased TL1A expression and have a higher risk of small bowel surgery. Decoy Receptor 3 (DcR3), a known IBD susceptibility gene, is a decoy receptor that can neutralize pro-inflammatory ligands including, TL1A (TNFSF15).

BRIEF DESCRIPTION OF THE FIGURES

Exemplary embodiments are illustrated in referenced figures. It is intended that the embodiments and figures disclosed herein are to be considered illustrative rather than restrictive.

SUMMARY OF THE INVENTION

Figure 1:
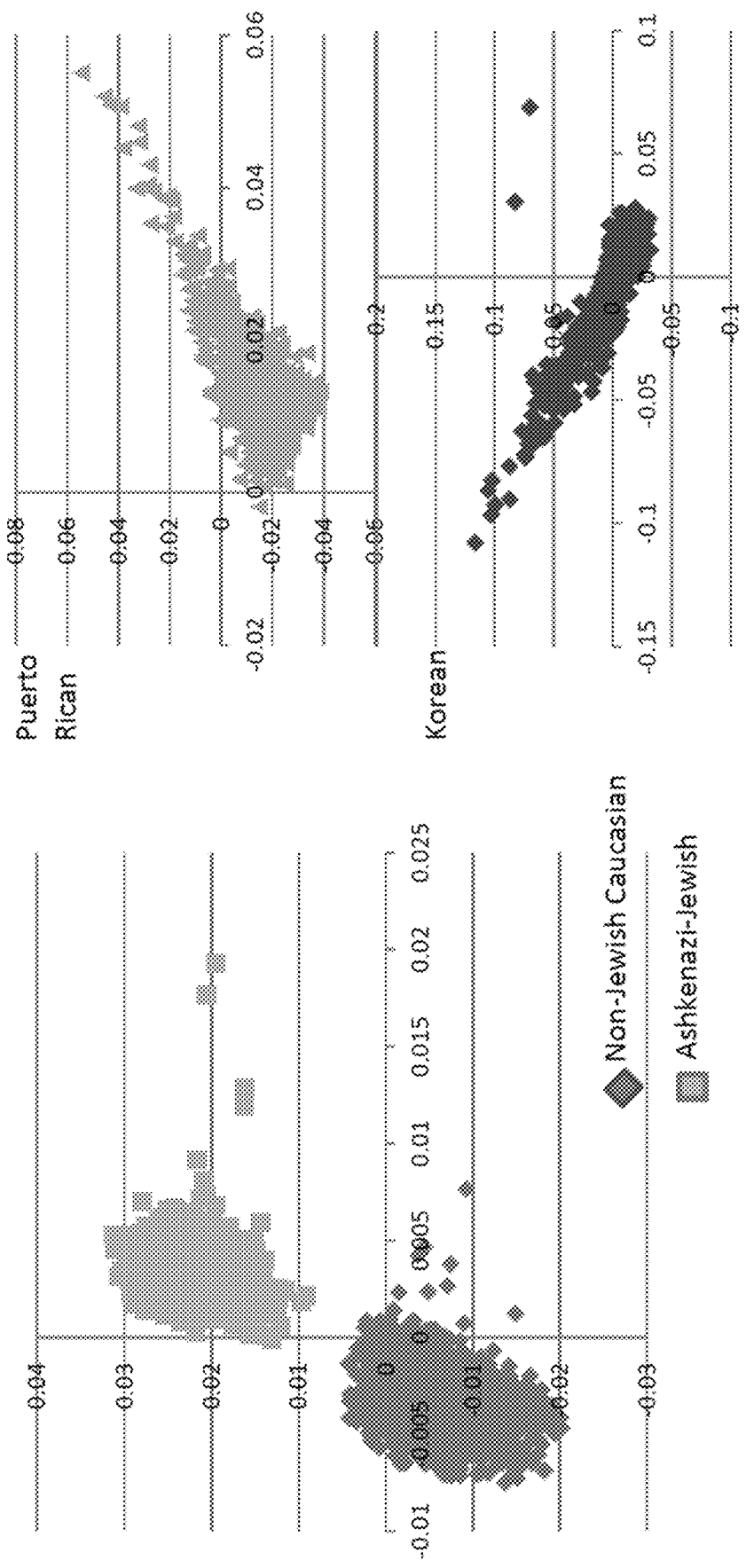
FIG. 1 depicts, in accordance with embodiments herein, principal component analysis (PC1/PC2).

Described herein is an assay for quantifying risk in a subject to Crohn's disease and/or fibrosist, including obtaining a sample from a subject, subjecting the sample to a genotyping assay adapted to determine the presence or absence of one or more variants at the TNFSF15 and/or DcR3 genetic loci, and quantifying risk in a subject to Crohn's disease and/or fibrosis based on the presence of one or more variants at the TNFSF15 and/or DcR3genetic loci. In various embodiments, the variants include one or more variants selected from the group including: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, and SEQ ID NO. 26. In other embodiments, the variants are SEQ ID NO. 3 and/or SEQ ID NO. 13. In other embodiments, the variant is SEQ ID NO. 22. In other embodiments, the subject is non-Jewish Caucasian, Ashkenazi, South Korean and/or Puerto Rican. In other embodiments, the subject is South Korean and the variant are SEQ ID NO. 3, SEQ ID NO. 13 and/or SEQ ID NO. 22. In other embodiments, the variant is a risk variant. In other embodiments, the variant is a protective variant. In other embodiments, the protective variant quantifies a reduced risk in the subject for structuring, CD, small bowel involvement and/or need for surgical intervention.

Also described herein is a method of diagnosing susceptibility to Crohn's disease and/or fibrosis in a subject, including obtaining a sample from a subject, subjecting the sample to a genotyping assay adapted to determine the presence or absence of one or more variants at the TNFSF15 and/or DcR3 genetic loci, and diagnosing susceptibility to Crohn's disease and/or fibrosis in the subject based on the presence of one or more variants at the TNFSF15 and/or DcR3 genetic loci. In other embodiments, variants consist of one or more variants selected from the group including: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, and SEQ ID NO. 26. In other embodiments, variants are SEQ ID NO. 3 and/or SEQ ID NO. 13. In other embodiments, variant is SEQ ID NO. 22. In other embodiments, subject is non-Jewish Caucasian, Ashkenazi, South Korean and/or Puerto Rican. In other embodiments, subject is South Korean and the variant are SEQ ID NO. 3, SEQ ID NO. 13 and/or SEQ ID NO. 22.

Also described herein is a method of treating Crohn's disease and/or fibrosis in a subject, including obtaining a sample from the subject, subjecting the sample to a genotyping assay adapted to determine the presence of one or more variants at the TNFSF15 and/or DcR3 genetic loci, and treating the Crohn's disease and/or fibrosis. In one embodiment, the variants consist of one or more variants selected from the group including: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, and SEQ ID NO. 26.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

As disclosed herein, the inventors examined the effect of T-helper pathway on TL1A induced colitis, and the effect of T-helper pathway on TL1A induced gut fibrosis. A role for TL1A in gut mucosal inflammation is highlighted by the finding that neutralizing TL1A antibody prevented and treated chronic colitis in mice. However, the contribution of either lymphoid or myeloid derived TL1A to the development of gut inflammation is not fully known. TL1A is the product of the TNFSF15 gene that is expressed by both lymphoid and myeloid derived cells. Variants in the TNFSF15 gene have been found to be associated with IBD. The protein product of TNFSF15, TL1A, is elevated in the intestinal mucosa of IBD patients. Certain TNFSF15 haplotypes are associated with susceptibility in non-Jewish Caucasian CD and UC. In addition, TNFSF15 haplotype B is not only associated with risk, but also with severity in Jewish CD patients. Moreover, monocytes from Jewish patients carrying the risk haplotype B express higher levels of TL1A in response to FcγR stimulation. These results show that CD associated TNFSF15 genetic variations contribute to enhanced induction of TL1A, resulting in severe, chronic mucosal inflammation and that modulation of TL1A may be a potential target for therapeutic development. TL1A signals via death domain receptor 3 (DR3) and several studies implicate the TL1A/DR3 signaling pathway in mucosal inflammation. Neutralizing TL1A-antibody ameliorates inflammation in DSS and Gαi2−/− T cell transfer chronic colitis models. Constitutive TL1A expression in mice leads to mild spontaneous ileitis and increased collagen deposition. TL1A modulates the adaptive immune response in the T-helper (Th)-1 effector arm, as shown by TL1A enhanced interferon (IFN)-γ production from peripheral and mucosal T-cells. TL1A is a TNF superfamily member. Thus, in summary TNFSF15 SNPs are associated with IBD, TNFSF15 haplotype B has increased TL1A expression with a higher risk of small bowel surgery, and constitutive T11a expression in mice confers worsened murine ileo-cecal inflammation and intestinal fibrostenosis. While it is known TL1A can enhance Th1, Th2, and Th17 effector cell function, it is poorly understood which TL1A activated T-helper effector pathway induces intestinal inflammation and fibrosis. Thus, a critical scientific question is understanding the effect of T-helper pathway on TL1A induced colitis and effect of T-helper pathway on TL1A induced gut fibrosis.

As disclosed herein, the inventors performed trans-ethnic fine mapping across TNFSF15 and DcR3 in Caucasian, Puerto Rican, and Korean CD. The inventors identified associations with Non Jewish Caucasian (NJ) Crohn's disease (CD) and rare TNFSF15 variants. This association is independent of previously reported common variants. Also, these variants are much more common in the South Korean (SK) population, and also associated with SK CD. DcR3 is significantly associated with NJ CD, a finding replicated in SK and variation at this locus modifies stricturing phenotype.

Described herein is an assay for quantifying risk in a subject to Crohn's disease and/or fibrosist, including obtaining a sample from a subject, subjecting the sample to a genotyping assay adapted to determine the presence or absence of one or more variants at the TNFSF15 and/or DcR3 genetic loci, and quantifying risk in a subject to Crohn's disease and/or fibrosis based on the presence of one or more variants at the TNFSF15 and/or DcR3genetic loci. In various embodiments, the variants include one or more variants selected from the group including: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, and SEQ ID NO. 26. In other embodiments, the variants are SEQ ID NO. 3 and/or SEQ ID NO. 13. In other embodiments, the variant is SEQ ID NO. 22. In other embodiments, the subject is non-Jewish Caucasian, Ashkenazi, South Korean and/or Puerto Rican. In other embodiments, the subject is South Korean and the variant are SEQ ID NO. 3, SEQ ID NO. 13 and/or SEQ ID NO. 22. In other embodiments, the variant is a risk variant. In other embodiments, the variant is a protective variant. In other embodiments, the protective variant quantifies a reduced risk in the subject for structuring, CD, small bowel involvement and/or need for surgical intervention.

Also described herein is a method of diagnosing susceptibility to Crohn's disease and/or fibrosis in a subject, including obtaining a sample from a subject, subjecting the sample to a genotyping assay adapted to determine the presence or absence of one or more variants at the TNFSF15 and/or DcR3 genetic loci, and diagnosing susceptibility to Crohn's disease and/or fibrosis in the subject based on the presence of one or more variants at the TNFSF15 and/or DcR3 genetic loci. In other embodiments, variants consist of one or more variants selected from the group including: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, and SEQ ID NO. 26. In other embodiments, variants are SEQ ID NO. 3 and/or SEQ ID NO. 13. In other embodiments, variant is SEQ ID NO. 22. In other embodiments, subject is non-Jewish Caucasian, Ashkenazi, South Korean and/or Puerto Rican. In other embodiments, subject is South Korean and the variant are SEQ ID NO. 3, SEQ ID NO. 13 and/or SEQ ID NO. 22.

Also described herein is a method of treating Crohn's disease and/or fibrosis in a subject, including obtaining a sample from the subject, subjecting the sample to a genotyping assay adapted to determine the presence of one or more variants at the TNFSF15 and/or DcR3 genetic loci, and treating the Crohn's disease and/or fibrosis. In one embodiment, the variants consist of one or more variants selected from the group including: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, and SEQ ID NO. 26.

In one embodiment, the present invention provides a method of diagnosing susceptibility to Crohn's disease in a subject by obtaining a sample from the subject, assaying the sample to determine the presence or absence of one or more risk variants in the subject, and diagnosing susceptibility to Crohn's disease based on the presence of one or more risk variants. In another embodiment, the one or more risk variants are at the TNFSF15 and/or DcR3 genetic loci. In another embodiment, the one or more risk variants are described in Tables 2 and 3 herein. In another embodiment, the subject is Caucasian, Puerto Rican, or South Korean. In another embodiment, the subject is Non-Caucasian.

In one embodiment, the present invention provides a method of diagnosing a Crohn's disease subtype in a subject by obtaining a sample from the subject, assaying the sample to determine the presence or absence of one or more risk variants in the subject, and diagnosing the Crohn's disease subtype based on the presence of one or more risk variants. In another embodiment, the one or more risk variants are at the TNFSF15 and/or DcR3 genetic loci. In another embodiment, the one or more risk variants are described in Tables 2 and 3 herein. In another embodiment, the subject is Caucasian, Puerto Rican, or South Korean. In another embodiment, the subject is Non-Caucasian.

In one embodiment, the present invention provides a method of treating Crohn's disease in a subject by determining the presence of one or more one or more risk variants in the subject, and treating the subject. In another embodiment, the one or more risk variants are at the TNFSF15 and/or DcR3 genetic loci. In another embodiment, the one or more risk variants are described in Tables 2 and 3 herein. In another embodiment, the subject is Caucasian, Puerto Rican, or South Korean. In another embodiment, the subject is Non-Caucasian.

In one embodiment, the present invention provides a method of diagnosing susceptibility to fibrosis in a subject by obtaining a sample from the subject, assaying the sample to determine the presence or absence of one or more risk variants in the subject, and diagnosing susceptibility to fibrosis based on the presence of one or more risk variants. In another embodiment, the one or more risk variants are at the TNFSF15 and/or DcR3 genetic loci. In another embodiment, the one or more risk variants are described in Tables 2 and 3 herein. In another embodiment, the subject is Caucasian, Puerto Rican, or South Korean. In another embodiment, the subject is Non-Caucasian.

In one embodiment, the present invention provides a method of diagnosing a fibrosis subtype in a subject by obtaining a sample from the subject, assaying the sample to determine the presence or absence of one or more risk variants in the subject, and diagnosing the fibrosis subtype based on the presence of one or more risk variants. In another embodiment, the one or more risk variants are at the TNFSF15 and/or DcR3 genetic loci. In another embodiment, the one or more risk variants are described in Tables 2 and 3 herein. In another embodiment, the subject is Caucasian, Puerto Rican, or South Korean. In another embodiment, the subject is Non-Caucasian.

In one embodiment, the present invention provides a method of treating fibrosis in a subject by determining the presence of one or more one or more risk variants in the subject, and treating the subject. In another embodiment, the one or more risk variants are at the TNFSF15 and/or DcR3 genetic loci. In another embodiment, the one or more risk variants are described in Tables 2 and 3 herein. In another embodiment, the subject is Caucasian, Puerto Rican, or South Korean. In another embodiment, the subject is Non-Caucasian.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Methods

The inventors performed trans-ethnic fine mapping across TNFSF15 and DcR3 in Caucasian, Puerto Rican (PR) and South Korean (SK) CD. Immunochip genotyping as performed on the following populations presented in Table 1.

TABLE 1

| Study subjects by ethnicity | | |
|---|---|---|
| Population | CD | Control |
| Non-Jewish Caucasian (NJ) | 779 | 4182 |
| Ashkenazi Jewish (AJ) | 492 | 395 |
| Puerto Rican (PR) | 300 | 235 |
| South Korean (SK) | 729 | 469 |

To measure association of TNFSF15 (416 SNPs) and DcR3 (13 SNPs), logistic regression was applied after controlling for population structure using principal component analysis (PCA) (FIG. 1). The result pACTs function corrects for multiple testing. A value of pACTs<0.05 was considered as statistically significant. Thereafter, population attributable risk (PAR) of the associated TNFSF15-DcR3 pathway SNPs was calculated in each population, the results of which are shown in Tables 2-4.

TABLE 2

SNPs associated with NJ CD. (pACTs < 0.05)

| SNP | dbSNP | Location | A1 | A2 | CD (Allele 1 Frequency) | Control (Allele 1 Frequency) | P-Values | pACT | Odds Ratio |
|---|---|---|---|---|---|---|---|---|---|
| Rare variants | | | | | | | | | |
| TNFSF15-130 | rs4979462 [SEQ ID NO. 1] | INTRON | T | C | 0.64% | 0.11% | 4.89E−05 | 7.76E−03 | 6.62 |
| TNFSF15-150 | rs55768522 [SEQ ID NO. 2] | INTERGENIC | A | G | 0.58% | 0.07% | 4.12E−05 | 6.63E−03 | 8.95 |
| TNFSF15-160 | rs 1322057 [SEQ ID NO. 3] | INTERGENIC | G | A | 0.83% | 0.13% | 3.02E−06 | 5.23E−04 | 6.97 |
| TNFSF15-271 | rs76779588 [SEQ ID NO. 4] | INTERGENIC | T | C | 0.64% | 0.11% | 4.48E−05 | 7.14E−03 | 6.70 |
| Common variants | | | | | | | | | |
| TNFSF15-90 | rs4574921 [SEQ ID NO. 5] | INTERGENIC | T | C | 77.3% | 72.3% | 5.31E−05 | 8.38E−03 | 1.30 |
| TNFSF15-106 | rs10114470 [SEQ ID NO. 6] | INTERGENIC | C | T | 72.2% | 67.0% | 7.98E−05 | 1.24E−02 | 1.27 |
| TNFSF15-110 | rs3810936 [SEQ ID NO. 7] | CODING(SYN) | C | T | 72.1% | 67.1% | 1.42E−04 | 2.14E−02 | 1.26 |
| TNFSF15-111 | rs4246905 [SEQ ID NO. 8] | INTRON | C | T | 74.9% | 69.9% | 1.07E−04 | 1.61E−02 | 1.28 |
| TNFSF15-120 | rs6478108 [SEQ ID NO. 9] | INTRON | T | C | 70.2% | 65.1% | 1.11E−04 | 1.66E−02 | 1.26 |
| TNFSF15-134 | rs6478109 [SEQ ID NO. 10] | INTERGENIC | G | A | 71.0% | 66.3% | 3.25E−04 | 4.60E−02 | 1.24 |
| TNFSF15-137 | rs7848647 [SEQ ID NO. 11] | INTERGENIC | C | T | 71.2% | 66.3% | 1.55E−04 | 2.33E−02 | 1.26 |
| TNFSF15-144 | rs59418409 [SEQ ID NO. 12] | INTERGENIC | I | D | 74.3% | 69.2% | 1.05E−04 | 1.61E−02 | 1.27 |
| TNFSF15-164 | rs7869487 [SEQ ID NO. 13] | INTERGENIC | T | C | 72.8% | 67.6% | 7.26E−05 | 1.12E−02 | 1.28 |

TABLE 3

Association results of DcR3 gene in NJ CD

| SNP | dbSNP | Gene | Location | A1 | A2 | CD (Allele 1 Frequency) | Control (Allele 1 Frequency) | P-Values | pACT | Odds Ratio |
|---|---|---|---|---|---|---|---|---|---|---|
| DcR3-1 | rs6011033 [SEQ ID NO. 14] | RTEL1 | INTRON | G | A | 79.6% | 78.0% | 1.27E−01 | 5.90E−01 | 1.11 |
| DcR3-2 | rs80132799 [SEQ ID NO. 15] | RTEL1 | INTRON | C | T | 93.6% | 93.3% | 6.93E−01 | 6.93E−01 | 1.05 |
| DcR3-3 | rs34412639 [SEQ ID NO. 16] | RTEL1 | INTRON | C | A | 99.6% | 99.3% | 1.43E−01 | 5.07E−01 | 1.88 |
| DcR3-4 | rs2236507 [SEQ ID NO. 17] | RTEL1 | INTRON | C | G | 79.4% | 77.3% | 5.35E−02 | 3.23E−01 | 1.14 |
| DcR3-5 | rs74506932 [SEQ ID NO. 18] | RTEL1 | INTRON | T | C | 1.80% | 1.58% | 5.28E−01 | 7.76E−01 | 1.14 |
| DcR3-6 | rs2738787 [SEQ ID NO. 19] | TNFRSF6B | CODING | G | A | 92.5% | 91.7% | 3.36E−01 | 6.54E−01 | 1.11 |
| DcR3-7 | rs55765053 [SEQ ID NO. 20] | TNFRSF6B | CODING | T | C | 8.09% | 7.08% | 1.34E−01 | 5.52E−01 | 1.17 |
| DcR3-8 | rs1291205 [SEQ ID NO. 21] | TNFRSF6B | CODING | C | G | 78.4% | 76.2% | 5.02E−02 | 3.09E−01 | 1.14 |
| DcR3-9 | rs6062496 [SEQ ID NO. 22] | TNFRSF6B | INTRON | A | G | 59.3% | 54.8% | 5.83E−04 | 4.93E−03 | 1.22 |
| DcR3-10 | rs1291206 [SEQ ID NO. 23] | TNFRSF6B | INTRON | G | A | 78.4% | 76.2% | 4.88E−02 | 3.02E−01 | 1.14 |
| DcR3-11 | rs 1291208 [SEQ ID NO. 24] | ARFRP1 | INTRON | C | T | 92.4% | 91.7% | 3.66E−01 | 6.87E−01 | 1.10 |
| DcR3-12 | rs2738788 [SEQ ID NO. 25] | ARFRP1 | INTRON | A | G | 0.19% | 0.07% | 1.70E−01 | 4.87E−01 | 2.67 |
| DcR3-13 | rs2236508 [SEQ ID NO. 26] | ARFRP1 | INTRON | G | A | 78.6% | 76.7% | 8.49E−02 | 4.60E−01 | 1.12 |

TABLE 4A

Trans-ethnic allele frequences and results in SNPs associated with NJ-CD

| SNP | NJ CD | NJ Ctrl | AJ CD | AJ Ctrl | PR CD | PR Ctrl | SK CD | SK Ctrl |
|---|---|---|---|---|---|---|---|---|
| Rare Variants of TNFSF15 | | | | | | | | |
| TNFSF15-130 | 0.64% | 0.11% | 2.34% | 2.28% | 14.0% | 11.1% | 52.7% | 34.5% |
| TNFSF15-150 | 0.58% | 0.07% | 2.24% | 2.03% | 8.50% | 5.11% | 52.6% | 34.4% |
| TNFSF15-160 | 0.83% | 0.13% | 2.34% | 2.78% | 10.2% | 6.60% | 52.7% | 34.6% |
| TNFSF15-271 | 0.64% | 0.11% | 2.34% | 2.15% | 8.00% | 4.26% | 44.9% | 31.8% |
| Common Variants of TNFSF15 | | | | | | | | |
| TNFSF15-90 | 77.3% | 72.3% | 77.7% | 79.9% | 83.2% | 81.1% | 79.6% | 64.7% |
| TNFSF15-106 | 72.2% | 67.0% | 73.9% | 77.0% | 77.5% | 77.4% | 68.9% | 49.9% |
| TNFSF15-110 | 72.1% | 67.1% | 74.1% | 77.2% | 77.3% | 77.7% | 68.5% | 49.8% |
| TNFSF15-111 | 74.9% | 69.9% | 77.3% | 79.1% | 82.3% | 79.8% | 80.5% | 65.9% |
| TNFSF15-120 | 70.2% | 65.1% | 75.2% | 77.7% | 77.8% | 77.0% | 71.5% | 51.3% |
| TNFSF15-134 | 71.2% | 66.3% | 78.7% | 80.0% | 79.5% | 76.6% | 71.7% | 51.8% |
| TNFSF15-137 | 71.0% | 66.3% | 78.6% | 79.2% | 79.3% | 77.0% | 71.7% | 51.8% |
| TNFSF15-144 | 74.3% | 69.2% | 81.9% | 82.5% | 83.3% | 79.1% | 77.3% | 59.1% |
| TNFSF15-164 | 72.8% | 67.6% | 80.3% | 81.1% | 83.0% | 79.1% | 77.4% | 59.1% |
| DcR3 variant | | | | | | | | |
| DcR3-9 | 59.3% | 54.8% | 67.1% | 64.3% | 60.5% | 57.0% | 17.6% | 14.3% |

TABLE 4B

Trans-ethnic allele frequences and results in SNPs associated with NJ-CD

| SNP | NJ CD | NJ Ctrl | AJ CD | AJ Ctrl | PR CD | PR Ctrl | SK CD | SK Ctrl |
|---|---|---|---|---|---|---|---|---|
| Rare Variants of TNFSF15 | | | | | | | | |
| TNFSF15-130 | 4.89E−05 | 8.70E−01 | 1.54E−01 | 6.92E−17 | 6.62 | 1.05 | 1.31 | 2.10 |
| TNFSF15-150 | 4.12E−05 | 7.23E−01 | 3.10E−02 | 5.28E−17 | 8.95 | 1.13 | 1.75 | 2.12 |
| TNFSF15-160 | 3.02E−06 | 5.81E−01 | 3.19E−02 | 8.66E−17 | 6.97 | 0.84 | 1.67 | 2.10 |
| TNFSF15-271 | 4.48E−05 | 7.99E−01 | 1.25E−02 | 3.15E−10 | 6.70 | 1.09 | 2.02 | 1.76 |
| Common Variants of TNFSF15 | | | | | | | | |
| TNFSF15-90 | 5.31E−05 | 2.92E−01 | 3.70E−01 | 5.70E−16 | 1.30 | 0.88 | 1.15 | 2.26 |
| TNFSF15-106 | 7.98E−05 | 1.34E−01 | 9.96E−01 | 2.52E−19 | 1.27 | 0.84 | 1.00 | 2.26 |
| TNFSF15-110 | 1.42E−04 | 1.29E−01 | 8.91E−01 | 4.03E−19 | 1.26 | 0.84 | 0.98 | 2.25 |
| TNFSF15-111 | 1.07E−04 | 3.90E−01 | 3.06E−01 | 5.83E−16 | 1.28 | 0.90 | 1.17 | 2.30 |
| TNFSF15-120 | 1.11E−04 | 2.49E−01 | 7.65E−01 | 4.71E−22 | 1.26 | 0.88 | 1.04 | 2.46 |
| TNFSF15-134 | 1.55E−04 | 5.83E−01 | 2.74E−01 | 1.69E−21 | 1.26 | 0.94 | 1.17 | 2.42 |
| TNFSF15-137 | 3.25E−04 | 8.34E−01 | 3.84E−01 | 1.69E−21 | 1.24 | 0.98 | 1.14 | 2.42 |
| TNFSF15-144 | 1.05E−04 | 8.59E−01 | 9.14E−02 | 3.24E−21 | 1.27 | 0.98 | 1.29 | 2.55 |
| TNFSF15-164 | 7.26E−05 | 7.69E−01 | 1.24E−01 | 1.98E−21 | 1.28 | 0.96 | 1.26 | 2.56 |
| DcR3 variant | | | | | | | | |
| DcR3-9 | 5.83E−04 | 1.51E−01 | 2.49E−01 | 2.01E−02 | 1.22 | 1.16 | 1.16 | 1.32 |

TABLE 5

Conditional analysis of the associated TNFSF15 SNPs in NJ CD and SK CD

| SNP | P-value NJ | P-value SK | P-value on SNP 160 NJ | P-value on SNP 160 SK | P-value on SNP 164 NJ | P-value on SNP 164 SK | P-value on SNP 160 & 164 NJ | P-value on SNP 160 & 164 SK |
|---|---|---|---|---|---|---|---|---|
| Rare Variants of TNFSF15 | | | | | | | | |
| TNFSF15-130 | 4.89E−05 | 6.92E−17 | 8.18E−01 | 4.82E−01 | 1.12E−04 | 9.39E−04 | 7.83E−01 | 6.17E−01 |
| TNFSF15-150 | 4.12E−05 | 5.28E−17 | 4.37E−01 | 2.30E−01 | 9.92E−05 | 7.68E−04 | 4.87E−01 | 2.73E−01 |
| TNFSF15-160 | 3.02E−06 | 8.66E−17 | — | — | 7.83E−06 | 1.07E−03 | — | — |
| TNFSF15-271 | 4.48E−05 | 3.15E−10 | 8.11E−01 | 4.46E−01 | 1.04E−04 | 4.38E−02 | 8.47E−01 | 5.84E−01 |
| Common Variants of TNFSF15 | | | | | | | | |
| TNFSF15-90 | 5.31E−05 | 5.70E−16 | 1.07E−04 | 3.46E−06 | 1.10E−04 | 4.34E−01 | 1.20E−01 | 4.63E−01 |
| TNFSF15-106 | 7.98E−05 | 2.52E−19 | 1.75E−04 | 1.87E−06 | 1.61E−01 | 7.18E−04 | 1.87E−01 | 2.51E−02 |

TABLE 5-continued

Conditional analysis of the associated TNFSF15 SNPs in NJ CD and SK CD

| | P-value | | P-value on SNP 160 | | P-value on SNP 164 | | P-value on SNP 160 & 164 | |
|---|---|---|---|---|---|---|---|---|
| SNP | NJ | SK | NJ | SK | NJ | SK | NJ | SK |
| TNFSF15-110 | 1.42E−04 | 4.03E−19 | 3.05E−04 | 2.95E−06 | 2.42E−01 | 1.16E−03 | 2.77E−01 | 3.78E−02 |
| TNFSF15-111 | 1.05E−04 | 5.83E−16 | 2.09E−04 | 4.32E−06 | 2.69E−01 | 5.35E−01 | 2.81E−01 | 5.65E−01 |
| TNFSF15-120 | 1.11E−04 | 4.71E−22 | 2.54E−04 | 3.38E−08 | 6.21E−01 | 1.94E−03 | 6.91E−01 | 6.24E−02 |
| TNFSF15-134 | 3.25E−04 | 1.69E−21 | 5.02E−04 | 1.18E−07 | 8.35E−01 | 6.14E−03 | 7.55E−01 | 1.49E−01 |
| TNFSF15-137 | 1.55E−04 | 1.69E−21 | 3.38E−04 | 1.18E−07 | 5.28E−01 | 6.14E−03 | 5.81E−01 | 1.49E−01 |
| TNFSF15-144 | 1.07E−04 | 3.24E−21 | 2.09E−04 | 1.99E−08 | 8.08E−01 | 7.98E−01 | 7.88E−01 | 5.37E−01 |
| TNFSF15-164 | 7.26E−05 | 1.98E−21 | 1.54E−04 | 1.12E−08 | — | — | — | — |

TABLE 6

Su results of DcR3 gene in NJ CD

| | | n | | CD Risk Allele Freq | | | |
|---|---|---|---|---|---|---|---|
| SNP | Phenotype | (+) | (−) | (+) | (−) | P-Value | Odds Ratio |
| DcR3-9 | Surgery | 323 | 248 | 56.7% | 62.9% | 3.62E−02 | 0.77 |
| DcR3-9 | Stricturing CD (B2) | 229 | 293 | 56.1% | 63.3% | 2.95E−02 | 0.75 |
| DcR3-9 | SB involvement (L1 + L3) | 460 | 98 | 57.6% | 66.3% | 2.26E−02 | 0.68 |

TABLE 7

G x G interaction analysis with TNFSF15 and DcR3

| | P-values (SNP x SNP) | |
|---|---|---|
| | NJ CD | SK CD |
| SNP | DcR3-9 | |
| TNFSF15_160 | 0.175 | 0.607 |
| TNFSF15_164 | 0.523 | 0.742 |

TABLE 8

Population attributable risk of TNFSF15-DcR3 SNPs

| SNP | GENE | NJ CD | SK CD |
|---|---|---|---|
| TNFSF15-160 | TNFSF15 | 1.4% | 41.4% |
| TNFSF15-164 | TNFSF15 | 17.0% | 70.8% |
| DcR3-9 | DcR3 | 20.5% | 9.0% |
| TNFSF15-DcR3 3 SNPs | — | 32.3% | 76.4% |

Example 3

TNFSF15 Analysis

As shown by the above results, 4 rare variants and 9 common variants were significantly associated with NJ CD (Table 2). All 13 associations were replicated in SK CD (Table 4), but the rare variants were much more common in the SK population.

Figure 2:
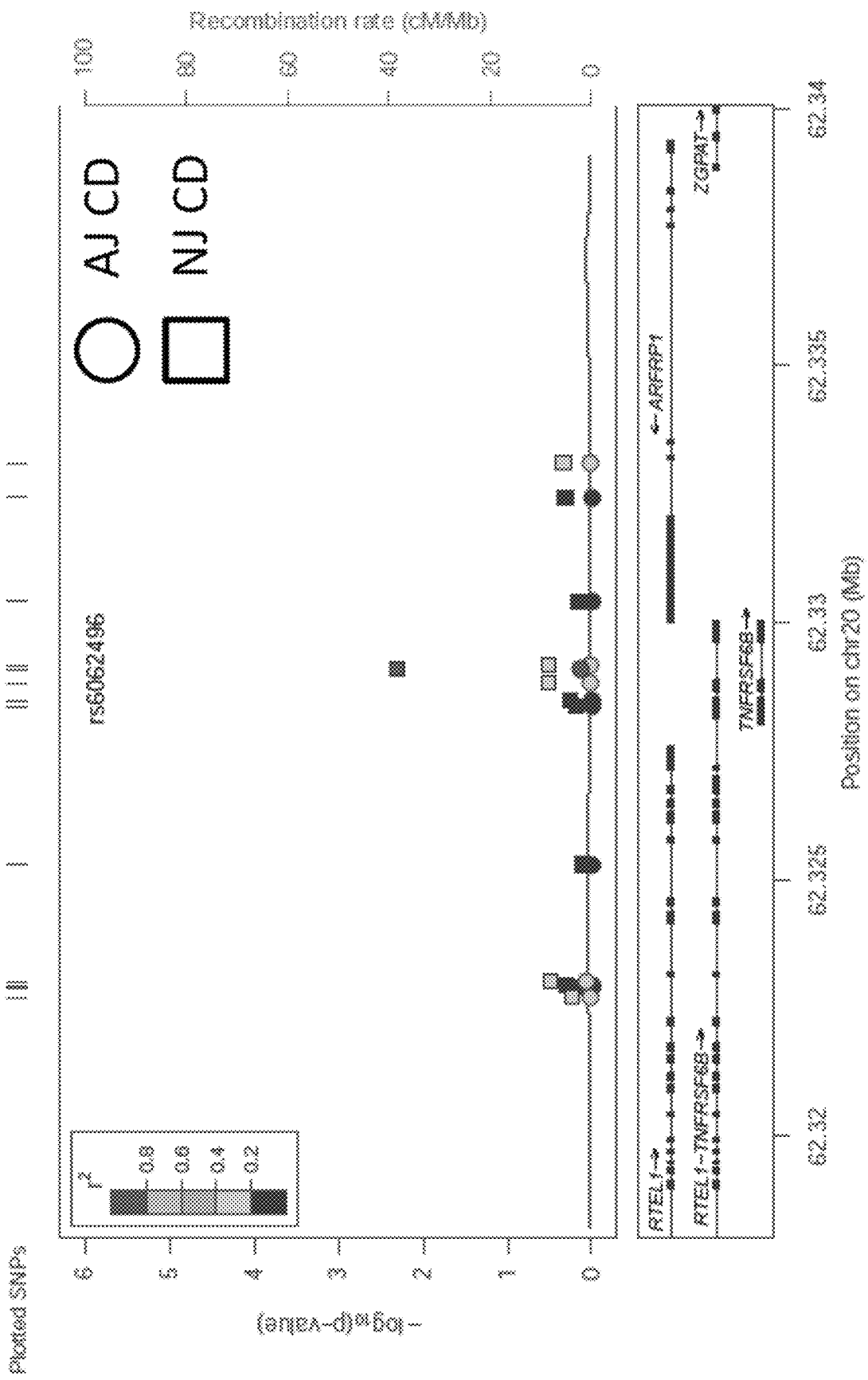
FIG. 2 depicts, in accordance with embodiments herein, pACTs of TNFSF15 region in NJ (Non-Jewish) and AJ (Ashkenazi Jewish) CD.
Figure 4:
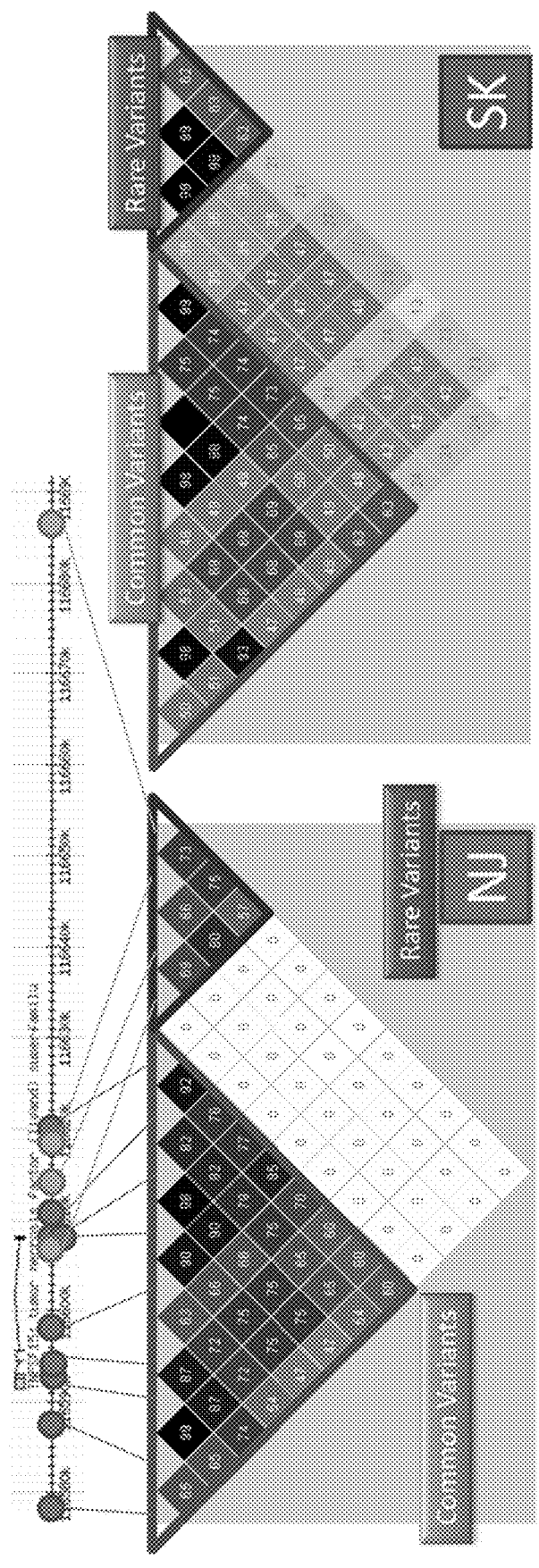
FIG. 4 depicts, in accordance with embodiments herein, linkage disequilibrium maps ($r^2$) of the associated TNFSF15 SNPs in NJ and SK.

Importantly, the 'rare' and 'common' variants can each be tagged by a single SNP (SNP160 & SNP164 respectively) in both NJ and SK. (Table 5, FIG. 4) The 'rare' variants were associated with CD in PR (at higher allele frequency). No association was seen in PR with the common variants. (Table 4). No significant SNP associations were observed in AJ CD. (FIG. 2, Table 4). After correcting for multiple comparisons there were no significant associations with rare or common CD-associated SNPs with clinical subphenotypes in NJ CD.

Example 4

DcR3 Analysis

Figure 3:
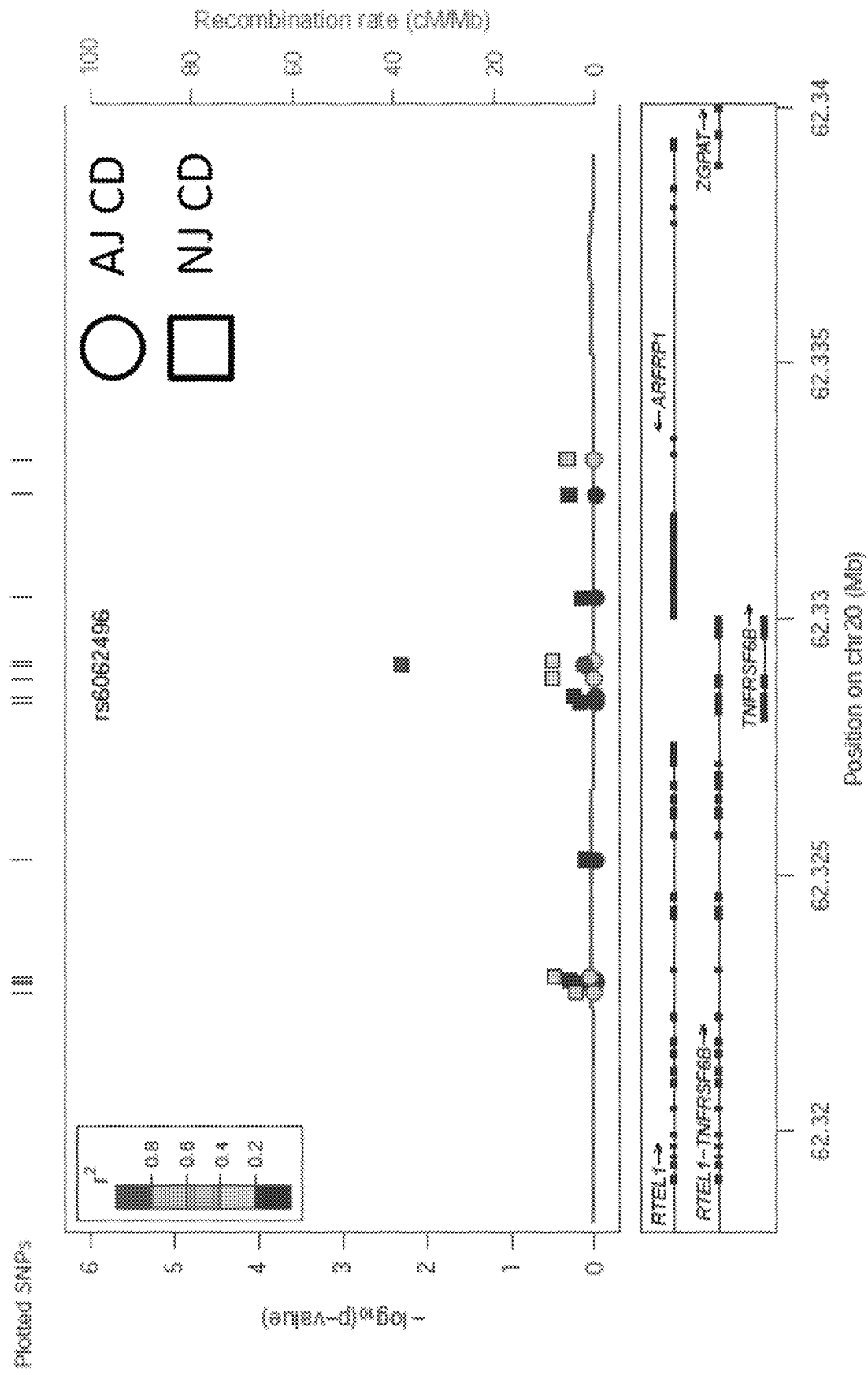
FIG. 3 depicts, in accordance with embodiments herein, pACTs of DcR3 (TNFRSF6B) region in NJ and AJ CD.

The above results further indicated that rs6062496 in intron 6 was significantly associated with NJ CD. (FIG. 3, Table 3). The association was confirmed in SK CD, but not in PR and AJ CD. (Table 4). It was further identified that rs6062496 also associated with protection against stricturing CD, small bowel involvement and need for surgery (Table 6).

Example 5

TNFSF15-DcR3 Analysis

The above results further suggest no significant DcR3 and TNFSF15 gene-gene interactions in NJ and SK. (Table 7). The PAR by TNFSF15-DcR3 pathway was 32.3% in NJ CD. (Table 8). The PAR by TNFSF15 variants in SK was the highest seen in either population explaining the dominant effect of this locus in Asian CD (Table 8)

Example 6

Conclusions

Based on the described results, the inventors identified associations with NJ CD and rare TNFSF15 variants. This association is independent of previously reported common variants. These variants are much more common in the SK population, and also associated with SK CD. DcR3 is significantly associated with NJ CD, a finding replicated in SK and variation at this locus modifies stricturing phenotype.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods of prognosis and diagnosis for inflammatory bowel disease related diseases and/or conditions, compositions of generated by the aforementioned techniques, treatment of diseases and/or conditions that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treating an inflammatory bowel disease (IBD) in a subject in need thereof, the method comprising administering to the subject an anti-tumor necrosis factor-like cytokine 1A (anti-TL1A) antibody, provided that the subject comprises a polymorphism in TNFSF15 at the position "N" within SEQ ID NO: 3, SEQ ID NO: 2, SEQ ID NO: 4, or a combination thereof, wherein the polymorphism within SEQ ID NO: 3 is a "G" allele; the polymorphism within SEQ ID NO: 2 is an "A" allele; and the polymorphism within SEQ ID NO: 4 is a "T" allele.

2. The method of claim 1, wherein the inflammatory bowel disease is Crohn's disease (CD).

3. The method of claim 1, provided that the subject further comprises a polymorphism in TNFSF15 within rs4979462.

4. The method of claim 1, provided that the subject is of Asian descent.

5. The method of claim 3, wherein the polymorphism in TNFSF15 within rs4979462 is a "T" allele.

* * * * *